United States Patent [19]

Ooms et al.

[11] Patent Number: 5,473,094
[45] Date of Patent: Dec. 5, 1995

[54] PROCESS FOR PREPARING ARYL CARBONATES

[75] Inventors: Pieter Ooms, Krefeld; Norbert Schön, Darmstadt; Hans-Josef Buysch, Krefeld, all of Germany

[73] Assignee: Bayer Aktiengesellschaft, Leverkusen, Germany

[21] Appl. No.: 271,488

[22] Filed: Jul. 7, 1994

[30] Foreign Application Priority Data

Jul. 19, 1993 [DE] Germany ............... 43 24 151.4

[51] Int. Cl.⁶ ...................................... C07C 69/96
[52] U.S. Cl. ................ 558/270; 558/271; 558/273; 558/274
[58] Field of Search ................... 558/270, 271, 558/273, 274

[56] References Cited

U.S. PATENT DOCUMENTS

| | | | |
|---|---|---|---|
| 2,362,865 | 11/1944 | Tryon et al. | 558/260 |
| 5,167,946 | 12/1992 | Mullins et al. | 558/274 |
| 5,239,105 | 8/1993 | Pews et al. | 558/274 |

*Primary Examiner*—José G. Dees
*Assistant Examiner*—Dwayne C. Jones
*Attorney, Agent, or Firm*—Connolly & Hutz

[57] ABSTRACT

Carbonates with aromatic ester groups may be prepared by reacting aromatic monohydroxy compounds with phosgene or with chloroformates of aromatic monohydroxy compounds, wherein reaction takes place at a temperature in the range 50° to 350° C. in the presence of aluminum oxides as heterogeneous catalysts.

9 Claims, No Drawings

PROCESS FOR PREPARING ARYL CARBONATES

FIELD OF THE INVENTION

The invention relates to a process for preparing carbonates with aromatic ester groups by reacting aromatic monohydroxy compounds with phosgene or chloroformates of aromatic monohydroxy compounds with the elimination of hydrogen chloride in the presence of aluminium oxides as heterogeneous catalysts.

BACKGROUND AND PRIOR ART

Carbonates with aromatic ester groups are suitable for preparing polycarbonates by the melt transesterification method, for preparing phenyl urethanes or are intermediates for active substances in the pharmaceutical and plant protection sector.

It is known that aryl carbonates may be obtained by phase interface phosgenation (Schotten-Baumann reaction) of aromatic hydroxy compounds. Here, the use of solvents and caustic soda solution is a disadvantage because partial saponification of phosgene or chloroformates can take place due to the presence of alkali. In all cases large amounts of common salt are obtained as a side product. Furthermore, care must be taken to recover the solvent.

Therefore condensation without the use of solvents in the presence of tetramethylammonium halides as catalysts has been suggested (U.S. Pat. No. 2,837,555). Here, the amounts of catalyst which are required are relatively large. In general, 5 to 7 wt. % of catalyst, with respect to the amount of phenol used, is needed in order to obtain economic rates of reaction. The reaction temperatures of 180° to 215° C. are linked with the risk of decomposition of the thermally labile tetramethyl ammonium halides. Furthermore, the catalyst has to be removed subsequently by washing with water, which makes its recovery much more difficult. In addition, far more than the stoichiometrically required amount of phosgene is consumed.

According to another process (U.S. Pat. No. 3,234,263), diaryl carbonates are obtained by heating phenyl chloroformates in the presence of large amounts of alkali (or alkaline earth) metal compounds using tertiary nitrogen bases as catalysts. However, this process has the disadvantage that elevated temperatures are used and the catalysts such as the alkali or alkaline earth metal compounds have to be partially dissolved in order to achieve only approximately economically acceptable reaction times. In this process half of the phosgene originally introduced is lost in the form of $CO_2$. In addition, the chloroformates have to be synthesised in a quite separate process step.

According to CA-A-2 058 359 (U.S. Pat. No. 5,167,946), diaryl carbonates are obtained by phosgenation of aromatic hydroxy compounds in the presence of aluminium compounds which are at least partially soluble under the reaction conditions, or are converted into soluble aluminium halides and obviously act as homogeneous catalysts in this form (cf. U.S. Pat. No. 2 362 865, col. 1, 1. 45 to 53). That is the reason why aluminium trichloride (solubility) is particularly preferred. Although very good yields are obtained, it is difficult to separate the catalysts from the products. In fact, it must be reckoned that these compounds have a certain degree of volatility and that thermal decomposition may take place due to these aluminium compounds, leading to impurities, reductions in quality and decreased yields. The same applies to the process in U.S. Pat. No. 2,362,865, which still mentions the use of titanium, iron, zinc and tin as the metals or in the form of their soluble salts, particularly the chlorides and phenolates.

Thus it seemed sensible to use heterogeneous, nonsoluble catalysts, which makes working up the reaction mixture a great deal easier. Proposals have also been put forward relating to this. Thus, the disclosure in EP-A-516 355 recommends in particular aluminium trifluoride, which is optionally applied to a support such as aluminosilicates. However, the synthesis of aluminium trifluoride is very complicated and expensive due to handling fluorine or hydrofluoric acid. Furthermore, metal salts on porous supports are described as catalysts for the reactions according to the invention in WO 91/06526. As can be seen from the test examples, fully continuous phosgenation of phenol on such catalysts was only possible in the gas phase, which is associated with relatively elevated reaction temperatures and the risk of decomposition of sensitive chloroformates. Obviously phosgenation of phenol with these catalysts cannot be performed in the liquid phase because the hot, liquid phenol washes out the active catalyst constituents.

SUMMARY OF THE INVENTION

The object of the invention therefore comprises the development of effective heterogeneous catalysts which are simpler to obtain.

It has now been found that aluminium oxides are outstanding catalysts for the reaction of phosgene or chloroformates with aromatic hydroxy compounds. This is particularly surprising and unexpected because such compounds are known to be inert according to the previous disclosure in WO 91/06526. Catalytic activity in the sense of the present invention is not reported. On the contrary, aluminium oxides are preferably mentioned as resistant and inert support materials.

Accordingly, the present invention provides a process for preparing aryl carbonates by reacting aromatic monohydroxy compounds with phosgene or chloroformates of aromatic monohydroxy compounds, which is characterised in that it is performed at temperatures in the range 50° to 350° C., optionally at a pressure of 0.2 to 20 bar in the presence of aluminium oxides as heterogeneous oxides.

DESCRIPTION OF PREFERRED EMBODIMENTS

The process according to the invention has the great advantage that the catalyst can be readily separated and no impurities remain in the crude reaction product. Therefore, working up is greatly simplified.

Aromatic monohydroxy compounds for the process according to the invention are those of the formula

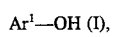

in which $Ar^1$ represents phenyl, naphthyl, anthryl, phenanthryl, indanyl, tetrahydronapthyl or the radical from a 5- or 6-membered aromatic heterocyclic compound with 1 or 2 hetero atoms from the group N, O and S, wherein these isocyclic and heterocyclic radicals may be substituted by 1 or 2 substituents such as straight-chain or branched $C_1$–$C_4$-alkyl groups, straight-chain or branched $C_1$–$C_4$-alkoxy groups, which may be substituted by phenyl, cyano and halogen (e.g. F, Cl, Br) and wherein furthermore the heterocyclic radical may be linked with a fused benzene ring.

Examples of aromatic monohydroxy compounds of the formula (I) are phenol, o-, m- and p-cresol, o-, m- and p-isopropylphenol, the corresponding halogeno or alkoxyphenols, such as p-chlorophenol or p-methoxyphenol, also monohydroxy compounds of naphthalene, anthracene and phenanthrene and furthermore 4-hydroxypyridine and hydroxyquinoline. Optionally substituted phenols are preferably used, quite particularly preferably phenol itself.

The process according to the invention may be performed with phosgene or with chloroformates of aromatic monohydroxy compounds. In the event that it is performed with phosgene, the chloroformate is produced initially and this then reacts further with the aromatic monohydroxy compound present in the reaction mixture to give a diaryl carbonate.

If chloroformates and an aromatic monohydroxy compound are used, symmetric or asymmetric carbonates may be produced.

Aromatic chloroformates which are suitable for the process according to the invention are thus those of the formula (II)

in which $Ar^1$ has the same meaning as given for formula (I).

Aluminium oxides which are suitable as heterogeneous catalysts may be present in crystalline form in various modifications, for example as $\alpha$-aluminium oxides, $\gamma$-aluminium oxides, $\eta$-aluminium oxides, $\kappa$-aluminium oxides and $\rho$-aluminium oxides, and may also contain amorphous fractions.

Such aluminium oxides and their source or the method of manufacture of this type of compound are described, for example, in Kirk-Othmer, Encyclopedia of Chemical Technology, 3rd ed., vol. 2, p. 218 ff., New York 1978 and Ullmann's Encyclopedia of Industrial Chemistry, 5th ed., vol Al, p. 557 ff. Weinheim 1985. Here, both aluminium oxides from natural sources, i.e. from various aluminium minerals, and also those from other aluminium intermediates such as aluminium salts, aluminium alkoxides and aluminium organo-compounds may be considered.

Aluminium oxides which are preferred in the sense of the invention are so-called "activated aluminium oxides", which are used, for example, as drying agents, adsorbents or catalyst supports. These may be amorphous, partly crystalline or crystalline (e.g. $\gamma$- and $\eta$-$Al_2O_3$). Furthermore, preferred aluminium oxides are also $\alpha$-aluminium oxides with BET surface areas $\geq 2$ $m^2$/g.

Naturally occurring or synthetic aluminium oxides may be used.

The aluminium oxides, preferably naturally occurring, may contain small amounts of other elements such as alkali and alkaline earth metals, iron or silicon. Products with amounts of such impurities of <2 wt. % are preferably used, particularly preferably <1 wt. %. Synthetic aluminium oxides are particularly pure. The aluminium oxides preferably have BET surface areas of 2 to 500 $m^2$/g, particularly preferably 4 to 450 $m^2$/g and quite particularly preferably 6 to 400 $m^2$/g. Acid, neutral and basic oxides may be used.

The catalysts may be used e.g. as powders or moulded items and are separated after reaction by means of e.g. filtration, sedimentation or centrifuging. In the event that a fixed bed arrangement is used, the aluminium oxides are preferably used as moulded items, e.g. as spheres, cylinders, rods, hollow cylinders, rings, etc.

When working with a suspended catalyst in stirred vessels or bubble columns the aluminium oxide catalysts are used in amounts of 0.5 to 100 wt. %, preferably 5 to 100 wt. % and particularly preferably 5 to 50 wt. %, with reference to the amount of monohydroxy compound used.

In the case of a continuous method of working in a co- or counter-stream or in the trickle phase on a fixed bed catalyst, catalyst loads of 0.1 to 20 g of aromatic hydroxy compound per g of catalyst per hour, preferably 0.2 to 10 $g.g^{-1}.h^{-1}$ and particularly preferably 0.2 to 5 $g.g^{-1}.h^{-1}$, are used.

Aluminium oxides used in batchwise tests may be used again without purification when using the same feed material. If the feed material is changed, the aluminium oxides are conveniently purified by extraction using inert solvents such as, for example, are mentioned below as reaction media, or using alcohols such as methanol, ethanol, isopropanol or butanol, using esters or amides of acetic acid or by treatment with superheated steam or air.

When working continuously, the aluminium oxides used may remain in the reactor for a long time. Regeneration may optionally be performed by the passage of superheated steam, optionally with the addition of small amounts of air (about 0.1 to 20 wt. %, with reference to the amount of steam used) at 150° to 800° C. or by the passage of diluting gases such as nitrogen or carbon dioxide which contain 0.01 to 20 wt. % of oxygen or by means of carbon dioxide on its own at 200° to 800° C. The preferred regeneration temperature is 250° to 700° C., particularly preferably 250° to 600° C.

The process according to the invention is performed at a temperature in the range 50° to 350° C., preferably 100 to 300° C., particularly preferably 100° to 250° C. The temperature may be altered within the range mentioned while performing the process according to the invention, in a preferred manner it is raised.

The process according to the invention is performed at a pressure of 0.2 to 20 bar, preferably 1 to 5 bar.

The process according to the invention may be performed using solvents such as aliphatic and aromatic hydrocarbons, such as pentane, hexane, octane, benzene, isomeric xylenes, diethylbenzene, alkylnaphthalenes, biphenyl; halogenated hydrocarbons, such as dichloromethane, trichloroethylene, etc.

The process is preferably performed in the melt by, for example, passing phosgene or a chloroformate of the formula (II) into a suspension of an aluminium oxide in a melt of the aromatic monohydroxy compound of the formula (I) and, after completion of reaction, separating the catalyst e.g. by filtering or centrifuging.

A further preferred embodiment of the synthesis is to blow phosgene or phosgene/hydrogen chloride mixtures or chloroformates of the formula (II) into a melt of the aromatic monohydroxy compound of the formula (I), with aluminium oxide catalyst suspended therein, in a continuously operating bubble column or bubble column cascade.

A further preferred mode of operation is the co-current process, in which aromatic hydroxy compounds of the formula (I) and phosgene or chloroformates of the formula (II) are applied in co-currents from above, for example, onto a catalyst packing arranged in a tube and hydrogen chloride and phosgenation products are withdrawn below at the foot of the tube.

A further preferred embodiment with particularly good results is to perform the reaction according to the invention in the trickle phase, wherein the aromatic monohydroxy compound of the formula (I) is added as a melt or in the form of a solution from above onto a bed of aluminium oxide and this liquid stream encounters a stream of phosgene or chloroformate flowing up from below. This embodiment is expediently performed in a vertical tube which may also contain intermediate partitions for improved distribution of the gas and liquid streams.

The reaction partners react in the molar ratio aromatic monohydroxy compound of the formula (I) to phosgene of 0.5 to 8:1, preferably 1.5 to 3:1. The equivalent molar ratio is 2:1 in this case.

In a corresponding manner, the aromatic monohydroxy compound reacts with a chloroformate in the molar ratio of 0.25 to 4:1, preferably 0.8 to 1.5:1. In this case the equivalent molar ratio is 1:1.

The crude aromatic carbonate obtained by heterogeneous catalysis is frequently very pure and may even be used in this form for many purposes, after degassing residual hydrogen chloride or other volatile substances. For applications with more stringent demands, the carbonate may optionally be further purified, e.g. by distillation or crystallisation.

EXAMPLES

Example 1

In a planar-section pot with flow-spoilers, a blower/stirrer and reflux condenser, 0.75 mol/h of phosgene was continuously bubbled into 141 g (1.50 mol) of phenol in the presence of 14.1 g (10 wt. % with reference to phenol) of a powdered aluminium oxide 507-C-I (neutral) from CAMAG. After about 2 h reaction time, the phenol conversion was 41%, wherein 66 g of diphenyl carbonate were formed. The selectivity to give carbonate was >99%.

Example 2

Example 1 was repeated at 140° C. using 14.1 g of aluminium oxide spheres A-2 from La Roche. After 2 h reaction time the phenol conversion was 11.9%, wherein 19.2 g of diphenyl carbonate were formed. The selectivity to give carbonate was greater than 99%.

Example 3

Example 1 was repeated at 140° C. using 14.1 g of γ-aluminium oxide spheres A-201 from La Roche. After 2 h reaction time the phenol conversion was 16.9%, wherein 27.1 g of diphenyl carbonate were formed. The selectivity to give carbonate was greater than 99%.

Example 4

Example 1 was repeated at 140° C. using 14.1 g of γ-aluminium oxide spheres SPH-501 from Rhone-Poulenc. After 2 h reaction time the phenol conversion was 20.0%, wherein 32.0 g of diphenyl carbonate were formed. The selectivity to give carbonate was greater than 99%.

Example 5

Example 1 was repeated at 140° C. using 14.1 g of γ-aluminium oxide spheres SPH-508 from Rhone-Poulenc. After 2 h reaction time the phenol conversion was 16.7%, wherein 26.8 g of diphenyl carbonate were formed. The selectivity to give carbonate was greater than 99%.

Example 6

Example 1 was repeated at 140° C. using 14.1 g of γ-aluminium oxide spheres SPH-512 from Rhone-Poulenc. After 2 h reaction time the phenol conversion was 15.8%, wherein 0.4 g of phenyl chloroformate and 25.1 g of diphenyl carbonate were formed. The selectivity to give carbonate and phenyl chloroformate was greater than 99%.

Example 7 (for comparison)

Example 1 was repeated at 140° C. without the addition of aluminium oxide. After 2 h reaction time the phenol conversion was less than 0.2%.

Example 8

In a 3-necked flask with thermometer and reflux condenser, a mixture of 9.4 g (0.10 mol) of phenol and 15.7 g (0.10 mol) of phenyl chloroformate was heated to 100° C. in the presence of 0.94 g (10 wt. % with reference to phenol) of a powdered aluminium oxide 507-C-I (neutral) from CAMAG. After 5 h reaction time, a phenol conversion of 38% to give diphenyl carbonate was found. Carbonate selectivity was >99%.

Example 9

Example 8 was repeated at 120° C. using the same catalyst. After 3 h reaction time the phenol conversion to give diphenyl carbonate was 79%. Carbonate selectivity was >99%.

Example 10

Example 8 was repeated at 140° C. using the same catalyst. After 1 h reaction time the phenol conversion to give diphenyl carbonate was 90%. Carbonate selectivity was >99%.

Example 11

Example 8 was repeated at 160° C. using the same catalyst. After 1 h reaction time the phenol conversion to give diphenyl carbonate was 99%. Carbonate selectivity was >99%.

Example 12

Example 8 was repeated at 140° C. using 0.94 g of a spherical aluminium oxide A-2 from La Roche. After 0.5 h reaction time the phenol conversion to give diphenyl carbonate was 80%. Carbonate selectivity was >99%.

Example 13

Example 8 was repeated at 140° C. using 0.94 g of an aluminium oxide granulate (1–2 mm diameter) from Morton Thiokol. After 1 h reaction time the phenol conversion to give diphenyl carbonate was 74%. Carbonate selectivity was >99%.

Example 14

Example 8 was repeated at 140° C. using 0.94 g of an aluminium oxide granulate (3.2 mm diameter) from Morton Thiokol. After 3 h reaction time the phenol conversion to give diphenyl carbonate was 93%. Carbonate selectivity was >99%.

Example 15

Example 8 was repeated at 140° C. using 0.94 g of an aluminium oxide granulate Active A (2–5 mm diameter) from Rhone-Poulenc. After 1 h reaction time the phenol conversion to give diphenyl carbonate was 61%. Carbonate selectivity was >99%.

Example 16

Example 8 was repeated at 140° C. using 0.94 g of a spherical α-aluminium oxide SPH 512 (4–5 mm diameter) from Rhone-Poulenc. After 5 h reaction time the phenol conversion to give diphenyl carbonate was 55%. Carbonate selectivity was >99%.

Example 17

Example 8 was repeated at 160° C. using 0.94 g of a spherical aluminium oxide (1.4 mm diameter) from Condea. After 3 h reaction time the phenol conversion to give diphenyl carbonate was 81%, after 5 h it was 91%. Carbonate selectivity was >99%.

We claim:

1. A process for preparing aryl carbonates by reacting aromatic monohydroxy compounds with phosgene or chloroformates of aromatic monohydroxy compounds, characterised in that the reaction is performed at a temperature in the range 50° to 350° C., at a pressure of 0.2 to 20 bar in the presence of one or more aluminium oxides as heterogeneous catalysts.

2. A process according to claim 1, characterised in that one or more activated aluminium oxides or α-aluminium oxides with surface areas, determined by the BET method, of 2 to 500 $m^2/g$ are used as catalysts in amounts of 0.5 to 100 wt. %, with reference to the amount of monohydroxy compound, in methods of working which are not fully continuous or with loads of 0.1 to 20 g of monohydroxy compound per g of catalyst per hour in fully continuous methods of working.

3. The process according to claim 1, wherein the aluminum oxide is a natural or synthetic aluminum oxide.

4. The process according to claim 1, wherein the aluminum oxide is an activated aluminum oxide.

5. The process according to claim 1, wherein the aluminum oxide is an α-aluminum oxide.

6. The process according to claim 1, wherein the aluminum oxide is γ-aluminum oxide.

7. The process according to claim 1, wherein the aluminum oxide is η-aluminum oxide.

8. The process according to claim 1, wherein the aluminum oxide is χ-aluminum oxide.

9. The process according to claim 1, wherein the aluminum oxide is ρ-aluminum oxide.

* * * * *